United States Patent [19]

Silva et al.

[11] Patent Number: 5,007,919

[45] Date of Patent: Apr. 16, 1991

[54] METHOD AND APPARATUS FOR PATIENT PROTECTION AGAINST VESSEL RUPTURE FROM BALLOON-TIPPED CATHETERS

[76] Inventors: Fidel H. Silva, 967 E. Center Fork Cir., Sandy, Utah 84094; Dwayne R. Westenskow, 3439 Winesap, Salt Lake City, Utah 84121

[21] Appl. No.: 419,828

[22] Filed: Oct. 11, 1989

[51] Int. Cl.$^5$ .............................................. A61M 29/02
[52] U.S. Cl. ...................................... 606/194; 604/99; 604/121
[58] Field of Search .............................. 604/96–101, 604/118, 236, 246, 121, 280, 283; 606/191, 192–194, 196

[56] References Cited

U.S. PATENT DOCUMENTS

| | | | |
|---|---|---|---|
| 2,473,742 | 6/1949 | Auzin | 604/100 |
| 3,543,759 | 12/1970 | McWhorter | 604/100 |
| 3,799,172 | 3/1974 | Szpur | 604/105 |
| 3,905,361 | 9/1975 | Hewson et al. | 128/145.5 |
| 3,948,259 | 4/1976 | Boldoc et al. | 604/121 X |
| 3,978,863 | 9/1976 | Fettel et al. | 604/100 X |
| 4,093,484 | 6/1978 | Harrison et al. | 604/96 X |
| 4,116,201 | 9/1978 | Shah . | |
| 4,142,525 | 3/1979 | Binard et al. | 604/121 |
| 4,178,939 | 12/1979 | Stephens | 128/207.15 |
| 4,185,638 | 1/1980 | Bruner | 604/100 |
| 4,245,639 | 1/1981 | La Rosa | 604/97 |
| 4,370,982 | 2/1983 | Reilly | 188/348 |
| 4,439,185 | 3/1984 | Lundquist | 128/349 |
| 4,439,186 | 3/1984 | Kuhl | 604/99 |
| 4,552,558 | 11/1985 | Muto | 604/100 |
| 4,583,917 | 4/1986 | Shah | 417/63 |
| 4,583,974 | 4/1986 | Kokernak | 604/99 |
| 4,606,346 | 8/1986 | Berg et al. | 606/196 |
| 4,614,188 | 9/1986 | Buzell et al. | 604/97 X |
| 4,784,648 | 11/1988 | Singh et al. | 604/141 |
| 4,856,510 | 8/1989 | Kowalewski | 128/207.15 |

OTHER PUBLICATIONS

Bazell et al., French patent application 2313084, published 12/76.
Swan, H. J. C., Ganz W., Forrester, J. et al., "Catheterization of the Heart in Man with Use of a Flow Directed Balloon-Tipped Catheter" N Engl J Med 283:447–451, 1970.
Barash, P. G., Nardi, D., Hammond, G. et al., "Catheter-Induced Pulmonary Artery Perforation" J. Thorac Cardiovasc Surg 82:5–12, 1981.
McDonald, D. H. and Zaidean, Jr., "Swan-Ganz Catheter Placement: Relationship to Intra-Balloon Pressures" (Abstract) Anesthesiology 57:A24, 1982.
Hardy, J-F., Morissette, M., Taillefer, J. et al., "Pathophysiology of rupture of the Pulmonary Artery by Pulmonary Artery balloon-Tipped Catheters" Anesth Analg 62:925–930, 1983.
Hardy J-F and Taillefer, J. "Inflating Characteristics of Swan-Ganz Catheter Balloons: Clinical Considerations", Anesth Analg 62:363–364, 1983.
Durbin, C. G. and Johns, R. A. "Range of Pulmonary Artery Balloon Inflation Pressures"(Abstract) Anesthesiology 69:A230, 1988.

Primary Examiner—John D. Yasko
Assistant Examiner—Adam J. Cermak
Attorney, Agent, or Firm—Joseph A. Walkowski

[57] ABSTRACT

The present invention comprises a safety inflation apparatus for preventing full inflation of a catheter balloon in a small body cavity of lesser internal diameter than that of the fully-inflated catheter balloon. The present invention includes a safety reservoir which inflates to absorb excess fluid volume from a catheter inflation device (such as a syringe) when the catheter balloon comes into contact with the wall of the small cavity, thereby preventing damage to the cavity wall and injury to the patient. In one embodiment of the invention, sensors and associated electronic displays are employed to provide an indication of the operating state of the system as the catheter balloon is inflated.

15 Claims, 5 Drawing Sheets

METHOD AND APPARATUS FOR PATIENT PROTECTION AGAINST VESSEL RUPTURE FROM BALLOON-TIPPED CATHETERS

BACKGROUND OF THE INVENTION

The present invention relates generally to medical devices, and more particularly to a method and apparatus for preventing rupture of blood vessels resulting from inflation of catheter balloons.

The flow directed balloon-tipped pulmonary artery catheter was introduced in 1970. While permitting easy bedside monitoring of cardiac function in critically ill patients, this device has resulted in certain complications, some benign and self-limiting, and others more significant. The latter include arterial and ventricular arrhythmias, balloon rupture, pulmonary infraction, bacteremia and intracardiac knotting. Rupture of the pulmonary artery is generally viewed as the most serious complication associated with the use of these balloon-tipped catheters. This is particularly a problem in patients over the age of sixty years, in whom it is believed that reduced vessel elasticity and increased fragility of tissues reduce the vessel rupturing pressure below the normal inflation pressures of the catheter balloons.

An explanation of a procedure employed with balloon-tipped catheters will result in a better appreciation of the magnitude of the problem. Use of inflatable catheters to internally block various body passages is well known in the art. Pulmonary artery catheters having inflatable balloons at their distal ends have been utilized in hundreds of thousands of procedures. The balloon, which in its uninflated state approximates the diameter of the catheter about which it is disposed, is inflated when desired by a gas syringe connected to the balloon channel or lumen of the catheter, which extends from outside the patient's body to the balloon.

To employ the catheter, a sheath is inserted in a suitable vein, such as the jugular vein, and the tip of the catheter is inserted through the sheath into the vein, until it exits the sheath, whereupon the balloon is inflated to act as a float responding to blood flow to assist in drawing the catheter through the vein until the balloon reaches the pulmonary artery. At this point, the balloon becomes wedged in a branch of the artery, and when lodged in this manner may be utilized to monitor the so-called "wedge" pressure of the artery via an oscilloscope connected to sensors in the catheter, all of which is known in the art.

After an initial wedge pressure reading is taken, the balloon is deflated and the catheter normally left in place in anticipation of subsequent readings. It is to this portion of the procedure that it is believed most problems with vessel rupture are attributable, for the deflation of the balloon at the distal end or "tip" of the catheter permits the now-smaller diameter tip to drift or migrate into a smaller portion or branch of the artery. If the migration phenomenon occurs, when next balloon inflation is attempted, the balloon may be positioned in a vessel of smaller diameter and/or greater fragility than intended. As a result, the normal inflation pressure of the balloon is exceeded due to the inability of the balloon to expand to its normal inflated diameter when injected with its specified volume of gas. Such balloon over-pressuring can result in catastrophic failure (rupture) of the vessel, generally resulting in rapid death of the patient.

Undue resistance to inflation of the balloon, which may indicate that the catheter tip is located in a small vessel, is a reason to terminate inflation attempts. However, such resistance, which may be transmitted to the practitioner through the "feel" of the plunger of the syringe being utilized for inflation, is subtle and difficult to interpret. Since balloons by various manufacturers provide differing inherent resistance to inflation, resistance to inflation attributable to a balloon being wedged in a small vessel may not be recognized by the feel of the syringe. This problem is aggravated with the small syringes typically used to inflate catheter balloons, since high pressures are indistinguishable from normal pressures to the clinician due to the small cross-sectional area of the plunger provided for pressure feedback from the catheter.

Pulmonary artery catheters of different manufacturers have widely differing balloon inflation pressures due to variations in thickness and latex composition of the balloons. When a balloon does inflate inside a vessel, it tends to "pop open" at a particular threshold pressure. The stiffer the balloon, the higher is the threshold pressure, with an attendant greater likelihood of vessel damage.

The concept of a pressure relief valve or regulator was believed to be useful in reducing the risk of vessel damage due to high balloon pressures because there is generally a 500 mm Hg difference between the normal opening pressure of the balloon and the minimum rupture pressure of the vessel. Use of such a valve at the balloon inflation port of a catheter has been suggested, as in U.S. Pat. No. 4,439,185 in the context of a liquid-inflated vascular dilating catheter, but the pop-open effect of the balloon negates the usefulness of such a device. Specifically, as a balloon pops open and thereby increases its volume, the internal pressure of the syringe/catheter/balloon system falls. Therefore, a relief valve set above the balloon pop-open pressure provides no protection after the balloon has opened; if set below the pop-open pressure, the pressure relief valve would prevent balloon inflation. Moreover, a pressure relief valve does not give a visual warning to the user that the catheter balloon has been inflated in a small vessel. Gas from the inflation syringe or other means escapes through the valve, thus preventing high inflation pressures, but without notice. If the catheter is subsequently inadvertently drawn back slightly to a larger diameter vessel, as often happens due to the motion of the heart or the patient, the balloon to vessel wall seal is lost and cannot be re-established in the larger vessel because the air or other gas required to do so has previously been vented through the pressure relief valve and cannot be returned into the system.

The addition of a "dead space" or pressure absorption zone between the syringe and the inflation port, such as has been suggested in U.S. Pat. No. 4,795,431, can be of use in limiting the maximum balloon pressure, as can the use of smaller than recommended gas volume for inflation, but both have proven unsatisfactory. It has been empirically determined that devices incorporating dead spaces or pressure absorption zones actually aggravates the vessel damage due to overpressure in certain diameter vessels. Use of a smaller than recommended gas volume results in an interior wedge blockage of vessels and an undesirable portion of the catheter tip remains exposed, enhancing the potential for vessel perforation, especially during catheter insertion. If the catheter tip resides in a small vessel, dangerously high balloon pressures can still result, especially if the vessel's internal diameter is close to the balloon's pop-open diameter.

Other attempts to identify over-pressurization of catheter balloons include external indicators or monitors associated with the catheter, such as indicator or "signal" balloons to provide the syringe operator with a tactile indication of the inflation pressure of the internal balloon, and pressure gauges. Both of these approaches, however, do not provide overpressure protection. At best they give a warning, but only after the patient has sustained significant injury from balloon inflation. Because of the pop-open effect of the balloon, a pressure gauge cannot indicate the actual pressure exerted on the vessel wall.

SUMMARY OF THE INVENTION

In contrast to the prior art, the present invention comprises a mechanically simple device of robust design which provides a fail-safe mechanism to prevent full inflation of a catheter balloon in a vessel smaller in internal diameter than that of the fully-inflated balloon.

The safety inflation apparatus of the present invention comprises a tubular conduit with a relief aperture extending through the wall thereof, and an inflatable elastomeric sleeve-like safety reservoir member stretched thereabout and sealed to the conduit on both sides of the aperture. One end of the conduit is adapted to receive fluid from a catheter balloon inflation device, such as a syringe, and the other end of the conduit is adapted to dispense fluid to the inlet of the balloon channel or lumen of a catheter. The safety reservoir member of the apparatus of the invention is slightly stiffer than the balloon of the catheter, so that the catheter balloon preferentially inflates first when located in a large vessel. However, if the vessel diameter is less than the normal inflated diameter of the catheter balloon, the catheter balloon expands only enough to contact the interior of the vessel wall, whereupon the safety reservoir member of the present invention inflates to absorb the excess fluid volume from the syringe, thereby preventing rupture of the vessel. Observation of the inflated safety balloon after syringe plunger deployment indicates to the operator that the catheter is in a smaller vessel. Although the wedge pressure is accurate and the patient's vessel has been protected, it may be important to retract and re-inflate the catheter in a larger vessel to prevent obstruction of the vessel by the catheter itself.

In one embodiment of the present invention, the conduit and safety balloon are housed in a simple cylindrical plastic housing having a first receptacle at the inlet end of the conduit to receive the luer connector or nozzle of a syringe and a second receptacle at the outlet end to connect to the catheter with which the invention is employed. The housing may be of clear non collapsible plastic and the balloon a bright color so that the state of the balloon may be readily ascertained. This embodiment of the device may be produced very cheaply, and utilized only on a single patient prior to disposal.

In another embodiment of the invention, the conduit and safety balloon have associated therewith a sensor to sense plunger position of the syringe, a pressure sensor to sense leaks in the system as the plunger is deployed, and an inflation sensor for the safety balloon, all connected to electronic display means for an immediate indication of the operating state of the system. In this more sophisticated embodiment, additional information beneficial to the safety of the patient is immediately available to the practitioner.

BRIEF DESCRIPTION OF THE DRAWINGS

The present invention will be more fully understood by one of ordinary skill of the art through a review of the following detailed description of the preferred embodiments of the invention taken in conjunction with the accompanying drawings, wherein.

DETAILED DESCRIPTION OF THE PREFERRED EMBODIMENTS OF THE INVENTION

Figure 1:
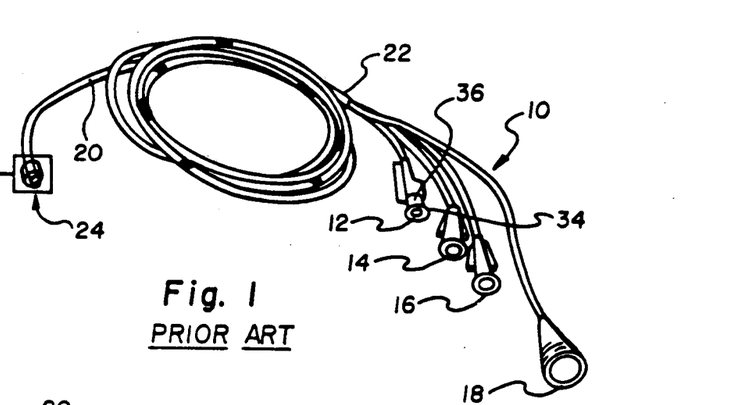
FIG. 1 depicts a balloon catheter of the type normally employed in pulmonary arteries.
Figure 1A:
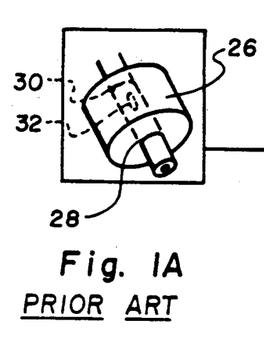
FIG. 1A comprises an enlarged view of the distal end of the catheter after the balloon is inflated.

FIGS. 1 and 1A of the drawings illustrate a balloon catheter 10 of the type generally referred to in the medical arts as a Swan-Ganz catheter after the physicians who introduced the device and the technique of employing it in pulmonary arterial monitoring. Such catheters are available from, among others, Edwards Laboratories, Inc., Santa Ana, Calif. Catheter 10 is of the quadruple channel or lumen design, having four lumens or tubes 12, 14, 16, and 18 at its proximal or inlet end. Lumens 12-18 feed into a single insertion tube 20 at junction 22. At the distal or innermost end 24 of insertion tube 20, a sleeve-like latex rubber catheter balloon 26 is disposed about tube 20 and sealed thereto at each end 28 and 30 of the balloon. Balloon 26 is inflated to its expanded diameter as shown in FIG. 1A via receipt of pressurized gas through lumen 12 and an internal passage (not shown) in insertion tube 20, which communicates with the interior of the balloon 26 through a small aperture 32 extending through the wall of the insertion tube 24. Lumens 14, 16 and 18 comprise, respectively, a proximal channel lumen, a distal channel lumen, and a thermistor lumen, all of which are conventional and are unrelated to the present invention.

Lumen 12 includes an inlet collar 36 having several tabs 34 adjacent its mouth, and a valve (unnumbered) to shut off gas flow to balloon 26. Conventionally, tabs 34 are utilized to secure collar 32 to the nozzle of a syringe. However, in the present invention, collar 32 is instead secured to the outlet of the housing for the safety balloon.

Figure 3A:
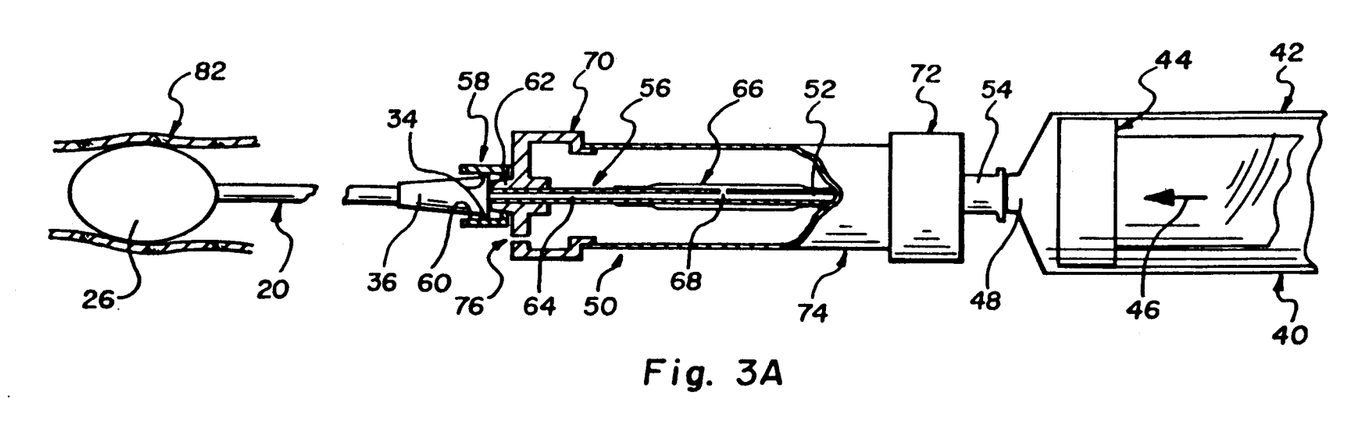
FIGS. 3A and 3B comprise partial sectional elevations of a first embodiment of the present invention showing operation of the invention when inflation of the catheter balloon is attempted in large and small vessels, respectively.
Figure 3B:
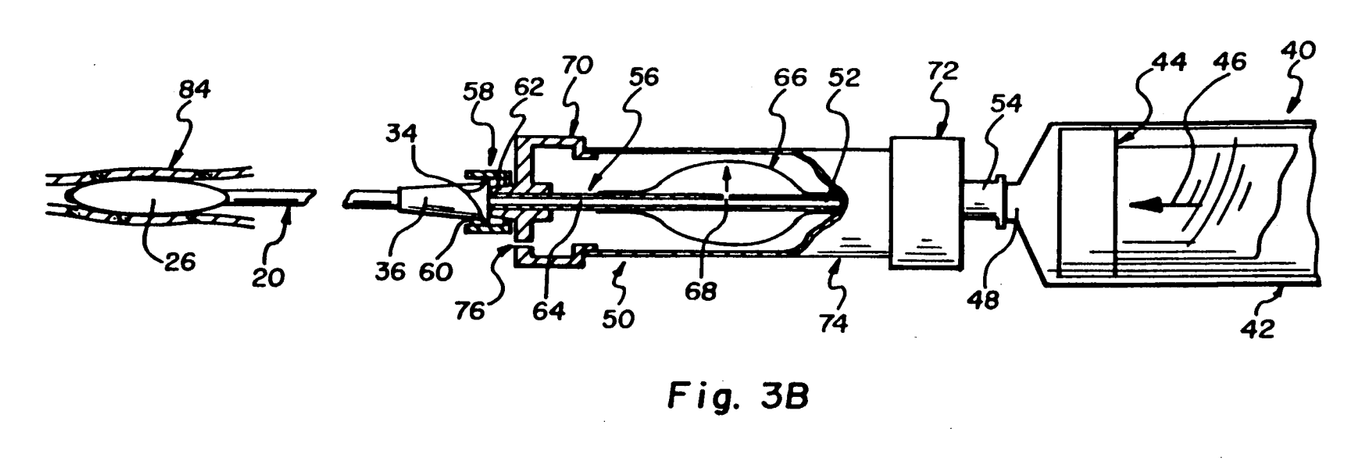

Referring to FIGS. 3A and 3B, catheter 10 is depicted schematically on the left-hand side of the drawings as a single channel extending from collar 36 via insertion tube 20 to catheter balloon 26. Syringe 40 having barrel 42 inside which plunger 44 may longitudinally move, is depicted schematically at the right side of the drawings, arrow 46 indicating the direction of plunger movement to feed gas to catheter balloon 26.

A first embodiment 50 of the safety inflation apparatus of the present invention is depicted in FIGS. 3A and 3B in series between collar 36 and syringe 40. Nozzle or luer connector 48 of syringe 40 is inserted in inlet receptacle 54 of apparatus 50 in communication and in sealing engagement with the inlet end 52 of tubular relief conduit 56. Collar 36 is inserted in outlet receptacle 58 and, via tabs 36 engaging with threads 60 on the inside of receptacle 58, balloon channel or lumen 12 is maintained in communication and sealing engagement with nozzle or luer connector 62 of apparatus 50 and thereby in communication with the outlet end 64 of relief conduit 56. Sleeve-like safety reservoir 66 is disposed about conduit 56 and is sealed thereto at each of its longitudinal ends. Reservoir inflation relief aperture 68 extends from the interior of conduit 56 through the wall thereof between the ends of safety reservoir 66. Safety reservoir 66 comprises an elastomer, preferably a latex composition, stretched to pre-load the sleeve in tension and to thereby minimize dead air space between the exterior of conduit 56 and the interior of safety reservoir 66, and to ensure a consistent, predictable predetermined inflation pressure.

As shown in FIGS. 3A and 3B, apparatus 50 may comprise a minimum number of parts in this preferred embodiment, the device then being inexpensive enough to produce so as to be disposable after a single use. Conduit 56 may be of plastic, with safety reservoir 66, comprising (as noted above) a latex compound sealed after pre-loading to the exterior of conduit 56 at each end of safety reservoir 66 via any means known in the art, including adhesive, heat-induced sealing or mechanical clamping. Nozzle 62 and receptacle 60 can be made integrally of plastic with outlet collar 70, and the assembly adhesively sealed about outlet end 64 of conduit 56. Inlet collar 72 and inlet receptacle 54 may be of similar integral design and plastic construction, and adhesively sealed about inlet end 52 of conduit 56. A noncollapsible cylindrical barrel 74, which may be of clear plastic or other material to facilitate viewing of the inflation state of safety reservoir 56, is adhesively secured between inlet collar 72 and outlet collar 70 about conduit 56 and safety reservoir 66. A small aperture 76 extends through the wall of outlet collar 70 to permit expansion of safety reservoir 66 without compression of the air inside barrel 74.

Figure 2A:
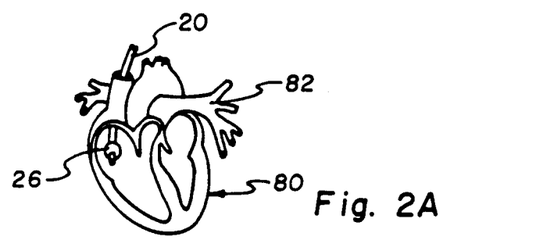
FIGS. 2A-2D illustrate catheter placement in the pulmonary system of a patient and the phenomenon of migration.
Figure 2B:
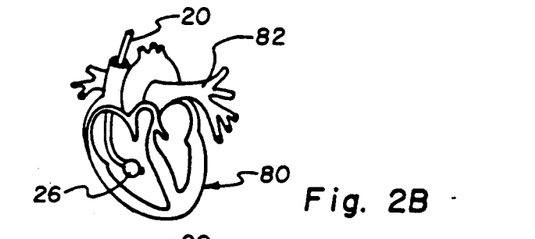
Figure 2C:
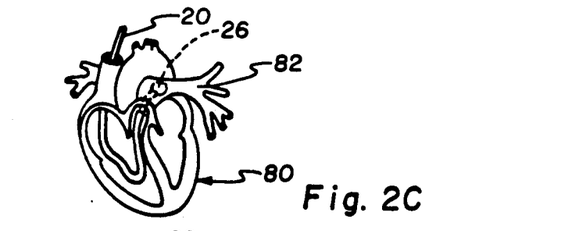

Safety reservoir 66, as shown in FIGS. 3A and 3B, is connected to the gas supply from syringe 40, in parallel to catheter balloon 26, and is slightly stiffer than the catheter balloon 26, so that when catheter balloon 26 is located in a large arterial vessel or is otherwise unconstrained, catheter balloon 26 responds to the inflation gas and inflates. In its open position, balloon 26 acts as a float, facilitating the passage of the catheter 10 through the heart 80 and into the pulmonary artery 82 (see FIGS. 2A through 2C). Turning again to FIG. 3A, catheter balloon 26 is shown "wedged" in pulmonary artery 82 in its fully inflated mode, whereupon pressure readings may be taken by the clinician. It should be observed that catheter balloon 26 is not imposing any substantial radial pressure, and thereby stress, on the walls of artery 82, as it contacts the vessel wall at a point of slight constriction after balloon inflation, acting as a plug or cork in the vessel.

Figure 2D:
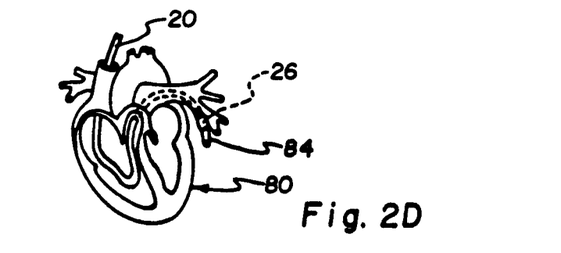

After an initial pressure reading has been taken by the clinician, it is established practice to deflate the catheter balloon 26 by opening the valve in collar 36 associated with lumen 12, in order to permit continued blood flow through the pulmonary system and specifically the pulmonary artery. However, re-instituted blood flow may tend to carry or "migrate" the distal end 24 of insertion tube 20 to a smaller vessel 84 (see FIG. 2D) downstream of the heart 80 and pulmonary artery 82. If insertion tube 20 so migrates, catheter balloon 26 is precariously located in a vessel 84 of much smaller diameter, in many instances of a diameter approximately the outer diameter of the uninflated balloon 26. When the clinician desires to re-inflate balloon 26 to take a second wedge-pressure reading, the constriction of the smaller vessel about the balloon will prevent or restrict inflation, resulting in an unintended pressure increase in balloon 26 and attendant stress on the vessel.

For example, if a 1.5 milliliter (ml) volume syringe is employed to inflate a catheter balloon of like normal inflation volume, and, due to constriction of the wall of small vessel 24 about a migrated balloon, the latter can be inflated to only 0.3 ml, under the gas equation for a constant temperature, $P_1 V_1 = P_2 V_2$, the pressure in the constricted catheter balloon 26 will be five times that in the syringe 40 when the plunger has been fully deployed, assuming no gas compression or internal volume expansion elsewhere in the catheter system. Even allowing for such compression or volume expansion, it is readily apparent that pressures in excess of the 900 mm Hg, known to cause vessel rupture in the pulmonary arterial system, may almost instantaneously be achieved. Laboratory testing has shown that pressures of at least 1100 mm Hg can easily be generated during balloon inflation. The resistance to internal pressure provided by the catheter balloon affords only minimal protection to the patient, absorbing only a small part of the 1100 mm Hg pressure, as the remaining pressure in the system is applied as a potentially injurious force directly to the confining vessel wall via the surface area of catheter balloon 26 in contact therewith.

When the apparatus of the present invention is introduced between syringe 40 or other inflation means and balloon channel or lumen 12, an altogether different result is obtained in the above-described situation. Safety reservoir 66 is designed to have an inflation pressure of 600 mm Hg or less, at least fifty percent (50%) lower than the 900 mm Hg; minimum vessel damage pressure. As syringe plunger 44 is deployed in barrel 42 of syringe 40, gas pressure is transmitted through relief conduit 56 into balloon channel or lumen 12, into insertion tube 20 and subsequently into catheter balloon 26 located in small vessel 84. Balloon 26 contacts the inner wall of vessel 84 in response to the gas pressure and, as noted above, is constrained against further inflation. Gas continues to be injected into the closed catheter system as deployment of plunger 44 is continued. However, as system pressure rises, gas is relieved through relief aperture 68 as safety reservoir 66 commences to inflate. The internal pressure in the system cannot exceed 600 mm Hg, the maximum pop-open pressure of the safety reservoir. Thus, any excess gas which cannot be accommodated in catheter balloon 26 due to the constraint of small vessel 84 is harmlessly relieved into safety reservoir 66, avoiding injury to the patient. Of course, when catheter re-inflation is attempted in a desired location, such as pulmonary artery 82 (see FIG. 2C), catheter balloon 26 inflates normally at a safe, low pressure, and safety reservoir 66 remains in its uninflated state.

Figure 4:
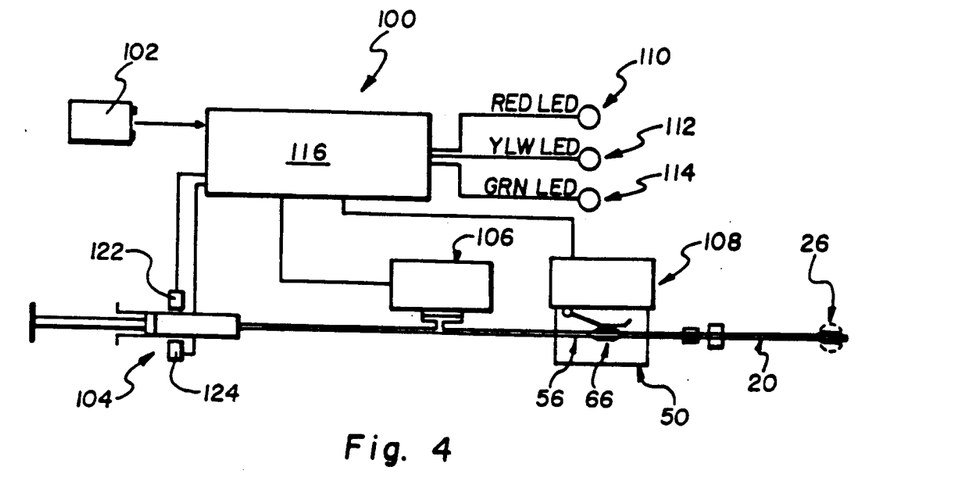
FIG. 4 comprises a schematic of a second embodiment of the invention employing electronic sensors.

Referring now to FIGS. 4A, 4B and 5, a second preferred embodiment 100 of the safety inflation apparatus of the present invention will be described. Embodiment 100 includes a relief conduit 56, relief aperture 68 and safety reservoir 66 identical to that of embodiment 50. In like manner, the inlet and outlet fittings to transmit gas to and from relief conduit 56 may be identical to that of the first embodiment, and so will not be further described, but the entire assembly will be referred to in FIG. 4 generally by reference numeral 50.

In addition to the previously described elements of assembly 50, embodiment 100 includes an electronic sensing and display means, powered by a power supply 102, preferably a 9 volt DC battery. The sensing means of embodiment 100 include plunger deployment sensor 104, pressure switch 106 and safety reservoir displacement switch 108. The display means of embodiment 100 includes a system leak or balloon rupture display 110, a small vessel display 112 indicative of the attempted inflation of a catheter balloon in a small vessel, and a balloon up display 114, indicative of proper inflation of the catheter balloon with no system leaks. Power supply 102 and all of the foregoing sensing and display means are interconnected by a circuit 116, primarily located on circuit card 118. Circuit 116 is shown schematically in FIG. 5 of the drawings, and the components thereof, including the sensing and display means of embodiment 100, will be hereinafter described in conjunction with the operation of embodiment 100.

When embodiment 100 is to be utilized in catheter balloon inflation, on/off switch 120 (see FIG. 5) for the electronics is switched to its "on" position, and syringe 40 is sealingly engaged with the inlet 52 of relief conduit 56 and catheter 10, specifically balloon channel 12, with the outlet 64 thereof. As plunger 44 is deployed, it passes between infrared emitter (LED) 122 of plunger deployment sensor 104, blocking the infrared waves previously sent to detector 124, which comprises a phototransistor. Prior to deployment of plunger 44, a completed circuit exists from power supply 102 through pressure switch 106, both via infrared LED 122 to ground 130 and via rheostat-type biasing resistor 128 and phototransistor detector 124 to ground 130. Switch 106 remains in the position shown in solid line in FIG. 5 until there is greater than 150 mm Hg pressure sensed in relief conduit 56.

After plunger 44 is deployed, the aforementioned circuit through phototransistor 124 is broken as phototransistor 124 becomes inoperative, no longer receiving infrared waves from emitter 122. This results in three possible alternative additional circuit paths from power supply 102 to ground 130, depending upon the existence of greater than 150 mm Hg pressure in relief conduit 56 and whether or not safety reservoir 66 is inflated. If there is no pressure or pressure less than 150 mm Hg in relief conduit 56, pressure switch 106 remains in the position shown in FIG. 5, and a circuit is completed via transistor 132, red LED 134 and buzzer 136 in parallel, and safety reservoir displacement switch 108 to ground 130. This circuit completion results in the activation of red LED 134 and of buzzer 136 of balloon rupture display 110, indicating rupture of catheter balloon 26 or other leak in the syringe/catheter system.

Figure 5:
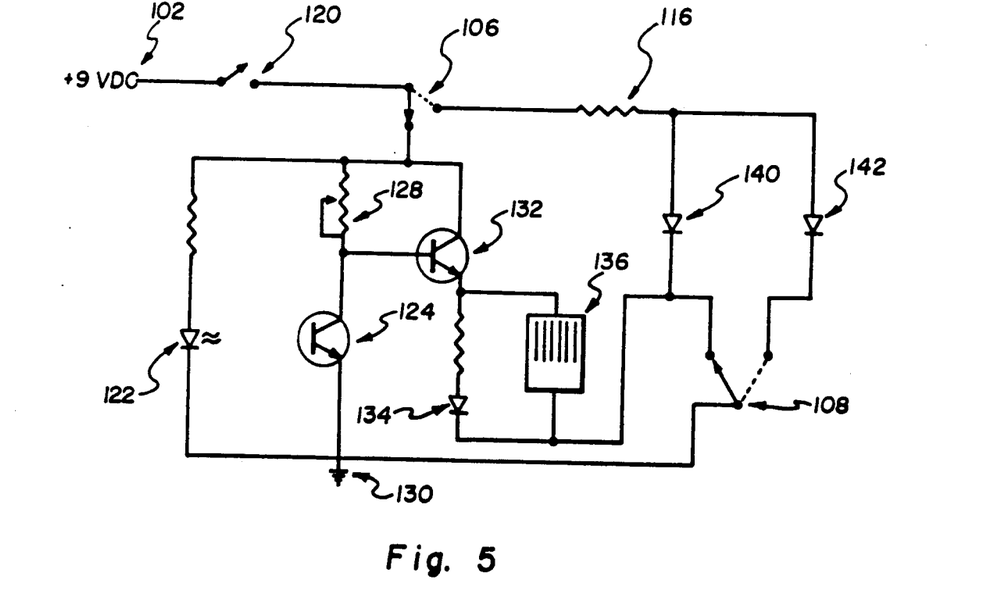
FIG. 5 comprises an electronic schematic for the second embodiment of the present invention.

If pressure switch 106 responds to an appropriate level of system pressure (>150 mm Hg), it moves to its dotted line position in FIG. 5, creating an alternate circuit path through either green LED 140, illumination thereof as balloon up display 114, indicating proper inflation of catheter balloon 26, or yellow LED 142, illumination thereof as small vessel display 112 being indicative of inflation of safety reservoir 66. The exact circuit path is dependent upon the position of safety reservoir displacement switch 108. If catheter balloon 26 is inflating normally, safety reservoir 66 will remain uninflated and displacement switch 108 will remain in its solid-line position as shown in FIG. 5, indicating to the practitioner that catheter balloon 26 is inflated and in a large vessel and all is well via the illumination of green LED 140 of balloon up display 114. If, however, catheter balloon 26 is in a small vessel which constrains its inflation, safety reservoir 66 inflates and displacement switch 108 is tripped by contact with the inflating balloon to its dotted-line position in FIG. 5, and the circuit is completed through yellow LED 142, of small vessel display 112, the illumination of LED 142 warning the practitioner that the catheter balloon is wedged in a small vessel.

The electronic components of the system have not been described in detail, because all are available at retail supply houses, such as Radio Shack, and the exact nature and specification of the power supply, LED's, phototransistor, transistor, buzzer, and resistors employed in the circuit are not material to the present invention and selection thereof is well within the skill of those in the art. Pressure switch 106 need only respond to an appropriate pressure level (150 mm Hg) and displacement switch 108 to movement of safety reservoir 66 as it inflates. However, it has been found that an especially suitable pressure switch is available as reference number F4400 pressure microswitch from Air Logic.

Referring now to FIGS. 6-10 of the drawings, the difference in inflation characteristics of a typical air-inflated pulmonary artery catheter balloon with and without the use of the present invention.

Figure 6:
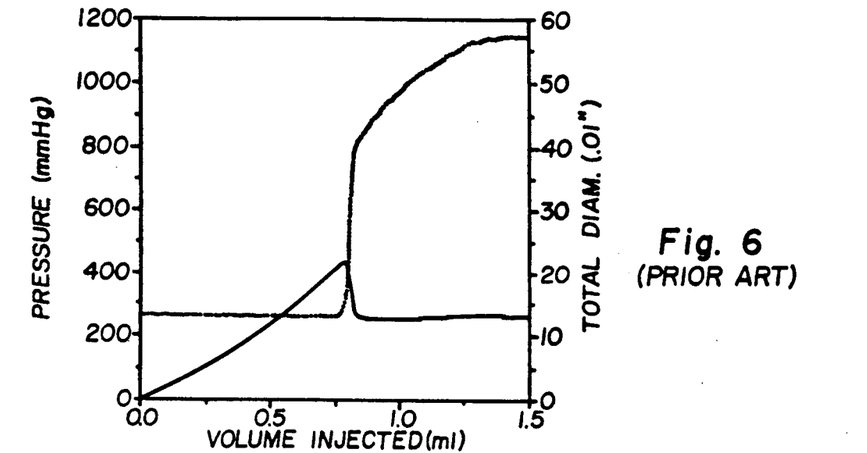
FIG. 6 is a graph depicting the inflation pressure/catheter balloon diameter relationship for an unconstrained balloon.

FIG. 6 shows the pressure to inflation diameter relationship for the above-referenced typical pulmonary artery catheter balloon as it is inflated to the recommended 1.5 ml inflation volume in an unconstrained state. As the first 0.75 ml of air is injected utilizing a syringe as previously described, internal balloon pressure rises from 0 to 450 mm Hg as the gas in the syringe and catheter lumen is compressed. During this phase there is no significant change in balloon volume, as evidenced by the dashed line on the graph. At a volume slightly greater than 0.75 ml, the balloon pop-open pressure is reached, the balloon rapidly expands, and pressure falls to about 260-270 mm Hg. As the syringe is further deployed and additional gas volume added, the balloon further expands with very little change in pressure.

Figure 7:
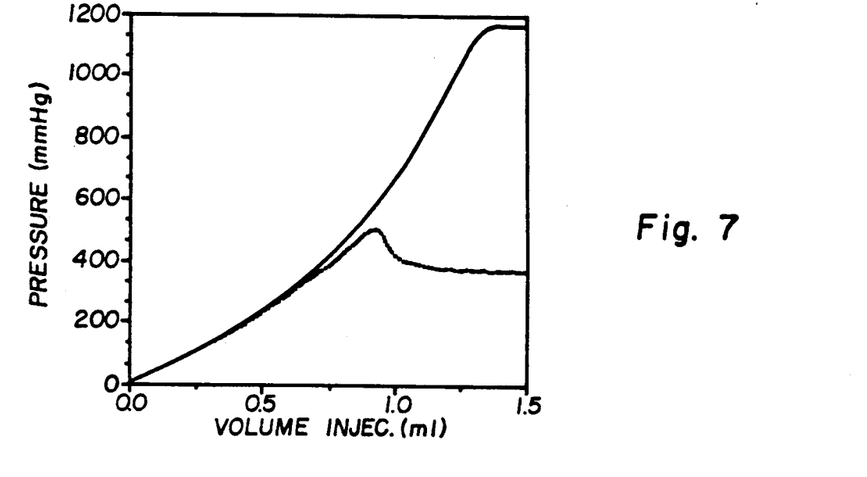
FIG. 7 is a graph depicting the inflation pressure/fluid injection volume relationship for a standard 1.5 ml catheter balloon inflated in a 0.15 inch diameter (I.D.) rigid-wall tube with (dashed line) and without (solid line) the use of the apparatus of the present invention.

Referring next to FIG. 7, the catheter balloon of FIG. 6 is next disposed inside a rigid tube of 0.15 inches diameter, simulating an inelastic small vessel such as might be found in an elderly patient. As 1.5 ml of gas is introduced into the catheter balloon, internal pressure (solid line) rises rapidly to almost 1200 mm Hg, due to the constraint of the surrounding tube. On the other hand, if the apparatus of the present invention is utilized with the catheter balloon as heretofore described, the injection of air results in a maximum system pressure (dashed line) of approximately 500 mm Hg, due to the accommodation of the excess pressure by the expansion of the safety reservoir of the present invention.

Figure 8:
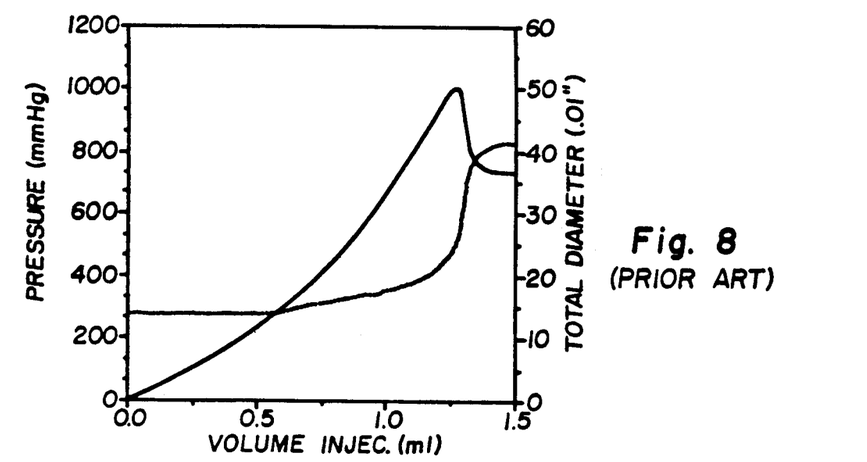
FIG. 8 is a graph depicting the inflation pressure (solid line) and corresponding diameter (dashed line) of a standard 1.5 ml catheter balloon as it is inflated in a 0.15 inch diameter latex tube.
Figure 9:
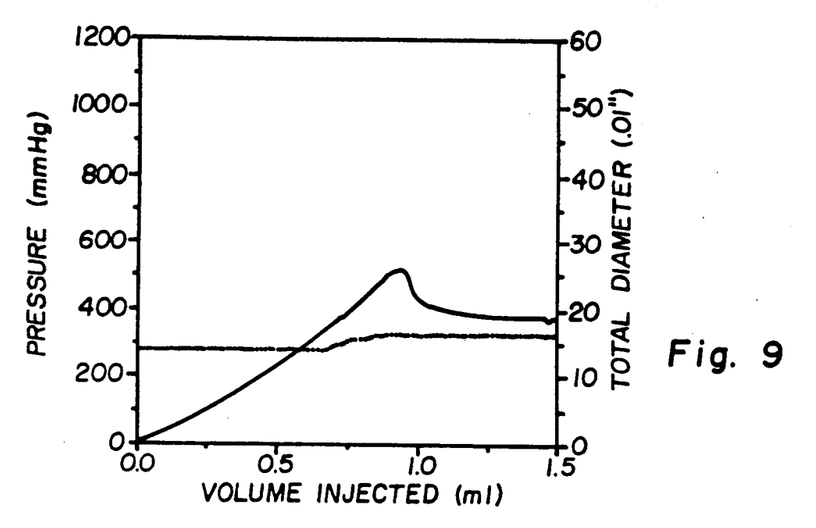
FIG. 9 is a graph depicting the inflation pressure (solid line) and corresponding diameter (dashed line) of a standard 1.5 ml catheter balloon as it is inflated in a 0.15 inch diameter latex tube using the apparatus of the present invention.

FIGS. 8 and 9 taken together provide another example of enhanced catheter balloon performance and system safety. Again, as in previous examples, a catheter balloon is inflated to 1.5 ml volume, but this time inside a 0.15 inch internal diameter latex tube, designed to simulate a vessel having some elasticity. In FIG. 8, the reader will note that the standard catheter balloon still reaches a maximum internal pressure (solid line) of about 1000 mm HG (versus almost 1200 mm Hg in FIG. 7) prior to falling to about 730 mm Hg as the balloon and latex vessel pop open and expand to a 0.40 inch final diameter. In FIG. 9, using the apparatus of the present invention, balloon pressure (solid line) reaches only a maximum of 525 mm Hg and a final diameter (dashed line) of 0.17 inches. The enhancement in patient safety is self-evident from the lower pressure and smaller diameter of the catheter balloon.

Figure 10:
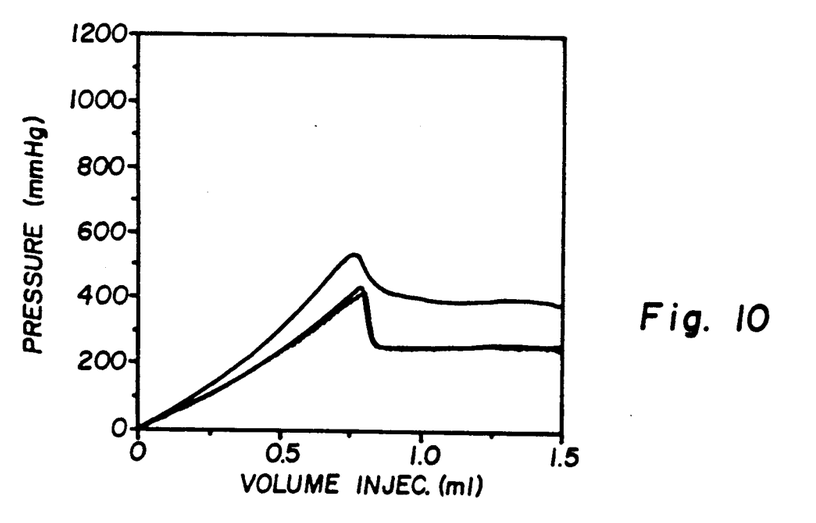
FIG. 10 is a graph of pressure versus injected volume of air for an unrestrained standard 1.5 ml catheter balloon (lower solid line), the apparatus of the present invention alone (top solid line), and the two utilized together (dashed line).

Finally, FIG. 10 depicts inflation pressure curves of a standard catheter balloon (thin lower solid line), the safety reservoir of the apparatus of the present invention (thick top solid line), and the pressure of the total system (dashed line) as described above, as the present invention is used in combination with the catheter as described above with an unrestrained catheter balloon. The standard balloon above reaches about 450 mm Hg maximum internal pressure as the system is injected with 1.5 ml of air. The safety reservoir of the present invention reaches about 550 mm Hg. The two in combination result in a system pressure of about 430 mm Hg due to the commencement of pressure accommodation by the safety reservoir.

Thus, it can be seen from the above graphic examples that the apparatus of the present invention has virtually no effect on catheter balloon performance if inflation thereof occurs in large vessels (FIG. 6) as the safety reservoir never comes into play, having a pop-open pressure greater than that of the catheter balloon. However, when the catheter balloon is constrained in a small vessel (FIGS. 7, 8, 9 and 10), a significant reduction in system pressure is effected using the present invention, with an attendant increase in patient safety.

To state the benefits of the present invention in another manner, utilization thereof provides a closed-system pressure relief mechanism which does not degrade the performance of a catheter balloon in its intended function, and accommodates catheter migration between large and small vessels while providing an inflation reserve. If the catheter balloon moves from a small vessel to a large one after the inflation gas is injected into the system, gas in the safety reservoir moves back into the now-unconstrained balloon due to its lower pop-open pressure, and expands the balloon to its inflated design diameter.

It has been established that the preferred inflation pressure for the safety reservoir of the present invention is about 100 mm Hg higher than that of the catheter balloon with which it is used. Thus, if catheter balloons of differing pop-open pressures from different manufacturers are to be utilized with the present invention, it is desirable to pre-load the safety reservoir sleeve of the present invention to an appropriate level and choose an appropriate safety reservoir sleeve material and wall thickness to provide a 100 mm Hg delta pressure.

While the preferred embodiments of the present invention employ sleeve-like safety reservoirs sealed to and surrounding coaxially disposed conduits, it is not so limited. For example, a sleeve or tube could be stretched (pre-loaded) at an angle away from the conduit and inflated at one end, the other being closed. A diaphragm could be pressure loaded at the outside to yield at a desired pressure in the system. Alternatively, a spring-loaded piston could be used in a cylindrical reservoir to accommodate excess pressure. However, all of the alternative embodiments described above are not preferred, due to their increased manufacturing cost, more variable pressure response characteristics, and in the latter case, frictional losses.

Thus, it is apparent that a novel and unobvious safety inflation apparatus has been developed for utilization with balloon catheters. While being described in the context of a Swan Ganz pulmonary artery catheter, it is not so limited, but may be employed with any type of fluid-inflated catheter. Many additions, deletions and modifications to the preferred embodiments as described herein will be readily apparent to and may be made by one of ordinary skill in the art without departing from the spirit and scope of the claimed invention.

We claim:

1. A method of safely introducing gas into a catheter balloon in a cavity in a patient, comprising:
    injecting said gas into said catheter balloon until internal balloon pressure reaches a first predetermined level;
    preventing pressure above that level in said balloon by relieving gas into a closed void exterior to the patient;
    sensing the pressure level of said injected gas; and
    indicating if said pressure does not reach a second predetermined level below said first predetermined level.

2. The method of claim 1, further comprising the additional steps of:
    moving said balloon into a larger cavity, thereby lowering said internal pressure below said first predetermined level; and
    inflating said catheter balloon to a larger diameter utilizing said relived gas from said closed void.

3. A safety inflation apparatus for use with a catheter including a catheter balloon disposed thereon, said catheter balloon having both a first predetermined inflation threshold pressure and a normal inflated diameter in a substantially externally unconstrained state, said apparatus being adapted to prevent damage to a body cavity of lesser internal diameter than said normal inflated diameter of said balloon when inflation of said catheter balloon within the external constraint of said body cavity is attempted, and said apparatus comprising:

relief conduit means having fluid inlet means adapted to receive fluid and fluid outlet means adapted to dispense said fluid through said catheter to said catheter balloon within said body cavity;

a fluid relief aperture in said conduit means between said fluid inlet means and said fluid outlet means communicating the interior of said relief conduit means with the exterior thereof; and safety reservoir means preloaded in tension against expansion, in communication with said relief conduit means through said relief aperture, and expandable at a second threshold pressure between that of said catheter balloon in its said substantially unconstrained state and that at which damage to said body cavity would normally result.

4. The apparatus of claim 3, wherein said safety reservoir means comprises an elastomeric compound.

5. The apparatus of claim 4, wherein said elastomeric compound comprises a latex compound.

6. The apparatus of claim 3, wherein said safety reservoir means is expandable at said second threshold pressure to accommodate the difference in fluid volume between that received from said catheter inflation device and that accepted by said constrained balloon.

7. The apparatus of claim 6, wherein said safety reservoir means comprises an elastomeric compound.

8. The apparatus of claim 7, wherein said elastomeric compound comprises a latex compound.

9. The apparatus of claim 3, wherein said relief conduit means is tubular, said relief aperture extends through the wall thereof, and said safety reservoir means comprises a sleeve-like member disposed about and sealed at its ends to said relief conduit means on either side of said relief aperture and between said fluid inlet means and said fluid outlet means.

10. The apparatus of claim 9, wherein said safety reservoir means comprises an elastomeric compound.

11. The apparatus of claim 10, wherein said elastomeric compound comprises a latex compound.

12. The apparatus of claim 9, further including a barrel disposed about said relief conduit means and surrounding said safety reservoir means in non-constraining relationship thereto.

13. The apparatus of claim 12, wherein said safety reservoir means comprises an elastomeric compound.

14. The apparatus of claim 13, wherein said elastomeric compound comprises a latex compound.

15. The apparatus of claim 3, wherein said safety reservoir means expansion threshold pressure is substantially less than 900 mg Hg.

* * * * *